United States Patent [19]

Yokoyama

[11] Patent Number: 4,826,854

[45] Date of Patent: May 2, 1989

[54] CERTAIN CYCLOALKA-(B)-PYRAZOLO(3,4-D)-PYRIDIN-3-ONE DERIVATIVES

[75] Inventor: Naokata Yokoyama, Cliffside Park, N.J.

[73] Assignee: Ciba-Geigy Corporation, Ardsley, N.Y.

[21] Appl. No.: 122,817

[22] Filed: Nov. 19, 1987

Related U.S. Application Data

[63] Continuation-in-part of Ser. No. 934,754, Nov. 25, 1986, abandoned.

[51] Int. Cl.$^4$ .................... A61K 31/44; C07D 471/04
[52] U.S. Cl. .................... 514/293; 514/269; 514/272; 514/273; 514/275; 514/278; 514/287; 514/300; 544/320; 544/321; 544/322; 544/331; 546/82; 546/118; 546/15; 546/64
[58] Field of Search ............ 546/82.118, 15, 64; 544/322, 331, 320, 321; 514/293, 269, 272, 273, 275, 278, 287, 300

[56] References Cited

U.S. PATENT DOCUMENTS

| | | | |
|---|---|---|---|
| 4,312,870 | 1/1982 | Yokoyama | 514/293 |
| 4,479,955 | 10/1984 | Yokoyama | 514/256 |
| 4,524,146 | 1/1985 | Yokoyama | 514/273 |
| 4,602,014 | 7/1986 | Yokoyama | 546/82 |
| 4,647,566 | 3/1987 | Yokoyama | 514/293 |
| 4,740,512 | 4/1988 | Yokoyama | 514/293 |

FOREIGN PATENT DOCUMENTS

| | | | |
|---|---|---|---|
| 0182165 | 5/1986 | European Pat. Off. | 546/82 |
| 851685 | 11/1985 | Greece | 546/82 |

OTHER PUBLICATIONS

Pharmacologist 28,112 (1986).
Bennett et al, "CGS 17867A: A non-Sedating Benzodiazephine Agonist" Aug. 18, 1986.
Drug Senelopment Research 6:313–325 (1985).
J. Med. Chem. 25, 337–339 (1982) Yokoyama et al.
J. Chem. Soc. Perkin I, 857 (1978) Kumar et al.

*Primary Examiner*—Mary C. Lee
*Assistant Examiner*—Zinna Northington
*Attorney, Agent, or Firm*—Norbert Gruenfeld

[57] ABSTRACT

Certain 8 to 12 membered cycloalka-[b]-pyrazolo[3,4,-d]-pyridin-3- one compounds which are useful as benzodiazepine receptor modulators are disclosed.

22 Claims, No Drawings

CERTAIN CYCLOALKA-(B)-PYRAZOLO(3,4-D)-PYRIDIN-3-ONE DERIVATIVES

CROSS REFERENCE TO RELATED APPLICATION

This application is a continuation-in-part of application Ser. No. 934,754 filed Nov. 25, 1986, now abandoned.

SUMMARY OF THE INVENTION

The present invention is directed to 2-substituted 8 to 12 membered cycloalka-[b]-ring-fused pyrazolo[3,4-d]-pyridin-3-ones which are benzodiazepine receptor ligands and modulators (antagonists, agonists or inverse agonists) demonstrating useful nervous system regulatory activity, e.g. psychoactive such as anxiomodulating activity.

The foregoing attributes render compounds of this invention particularly useful when administered, alone or in combination, to mammals for the treatment of e.g. nervous system disorders such as anxiety and convulsive conditions (epilepsy) for compounds which are predominantly benzodiazepine receptor agonists; or as enhancers of cognitive performance and of vigilance, as somnolytics, as appetite suppressants, as antagonists (antidotes) of the effects of benzodiazepine drug overdose on the central nervous system or as antagonists of the sedative effects of alcohol and benzodiazepine drugs in combination, for compounds which are predominantly benzodiazepine receptor antagonists/inverse agonists.

DETAILED DISCLOSURE OF THE INVENTION

This invention relates to certain novel 2-substituted- 8 to 12 membered cycloalka-[b]-ring-fused pyrazolo[3,4-d]pyridin-3-ones useful as e.g. benzodiazepine receptor modulators, processes for preparing the same, pharmaceutical compositions comprising said compounds and methods of treating e.g. nervous system disorders by administration of said compounds and compositions to mammals.

Particularly the invention relates to compounds of formula IA or IB

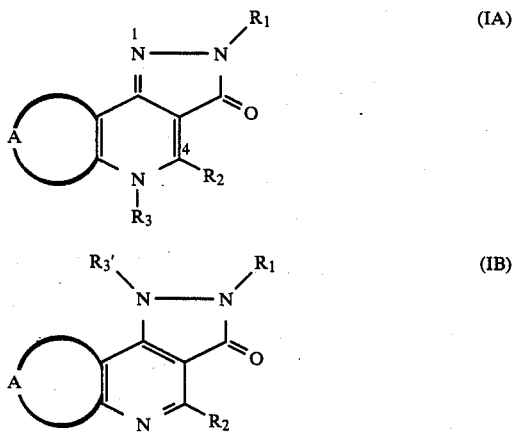

wherein A represents an optionally substituted saturated divalent grouping which together with the two carbon atoms to which it is attached represents a fused 8, 9, 10, 11 or 12 membered carbocyclic ring selected from cycloocteno, cyclononeno, cyclodeceno, cycloundeceno and cyclododeceno; each unsubstituted or mono- di-, tri- or tetra-substituted on carbon atoms within A by lower alkyl, lower alkylidene, $C_3$-$C_7$-cycloalkyl, hydroxy, acyloxy, oxo, lower alkoxy, aryl or aryl-lower alkoxy; and when disubstituted on the same carbon atom within A, said carbon atom in each ring is preferably substituted by two lower alkyl or two aryl-lower alkyl groups, or by one lower alkyl or aryl-lower alkyl group and one group selected from hydroxy, lower alkoxy, aryl-lower alkoxy and acyloxy groups; or each disubstituted on the same carbon atom within A by straight chain alkylene of 2 to 6 carbon atoms forming with the carbon to which the alkylene chain is attached a spiro-fused 3 to 7 membered ring; or each ring is disubstituted on adjacent carbon atoms by alkylene of 3,4 or 5 carbon atoms to form with the two adjacent carbon atoms to which said alkylene grouping is attached a fused 5-, 6- or 7-membered ring; $R_1$ represents lower alkyl, phenyl, or phenyl substituted by one or two radicals selected from lower alkyl, lower alkoxy, halogen and trifluoromethyl; or $R_1$ represents a five-membered unsaturated heterocyclic radical containing one hetero atom selected from sulfur, oxygen, and unsubstituted or lower alkyl substituted amino nitrogen, or a said radical containing two hetero atoms consisting of one imino nitrogen and one member selected from unsubstituted or lower alkyl substituted amino nitrogen, sulfur and oxygen; or $R_1$ represents an unsaturated six membered heterocyclic radical containing one or two nitrogen atoms; or $R_1$ represents a bicyclic benzo-fused five membered unsaturated heterocyclic radical containing one hetero atom selected from sulfur, oxygen and unsubstituted or lower alkyl substituted amino nitrogen; or $R_1$ represents a bicyclic benzo-fused five membered unsaturated heterocyclic radical containing two hetero atoms consisting of one imino nitrogen and one member selected from unsubstituted or lower alkyl substituted amino nitrogen, oxygen and sulfur; or $R_1$ represents a bicyclic benzo-fused 6-membered unsaturated heterocyclic radical containing one or two nitrogen atoms; or $R_1$ represents any of said heterocyclic radicals mono- or di-substituted on carbon by lower alkoxy, lower alkyl or halogen; $R_2$, $R_3$ and $R_3'$ independently represent hydrogen or lower alkyl; or tautomers thereof; or salts thereof, particularly pharmaceutically acceptable salts.

Preferred are the above compounds of formula IA or IB wherein $R_1$ represents lower alkyl, phenyl, or phenyl mono- or disubstituted by lower alkyl, lower alkoxy, halogen or trifluoromethyl; or $R_1$ represents an aromatic heterocyclic radical selected from pyridyl, quinolyl, isoquinolyl, pyrimidyl and thiazolyl, or any said heterocyclic radical mono- or di-substituted by lower alkyl, lower alkoxy or halogen; and $R_2$, $R_3$ and $R_3'$ independently represent hydrogen or lower alkyl; and pharmaceutically acceptable salts thereof.

Further preferred are said compounds of formula IA or IB wherein A together with the two carbon atoms to which it is attached represents a fused ring selected from cycloocteno, cyclononeno, cyclodeceno, cycloundeceno and cyclododeceno in which A represents hexamethylene, heptamethylene, octamethylene, nonamethylene or decamethylene respectively; each said ring unsubstituted or mono-, di-, tri- or tetra-substituted on carbon atoms within A by lower alkyl, lower alkylidene, $C_3$-$C_7$-cycloalkyl, hydroxy, acyloxy, oxo, lower alkoxy, aryl, aryl-lower alkyl or aryl-lower alkoxy; and when disubstituted on the same carbon atom within A, said carbon atom in each ring is preferably substituted by two lower alkyl or two aryl-lower alkyl groups, or by one lower alkyl or aryl-lower alkyl and one group selected from hydroxy, lower alkoxy, aryl-lower alkoxy and acyloxy groups; or each ring is disubstituted on the same crbon atom within A by ethylene, propylene, butylene or pentylene forming with the carbon to which the alkylene chain is attached a spiro fused cyclopropyl, cyclobutyl, cyclopentyl or cyclohexyl ring; or each ring is disubstituted on adjacent carbon atoms by propylene or butylene to form with the two adjacent carbon atoms to which said alkylene grouping is attached a fused cyclopentane or cyclohexane ring; $R_1$, $R_2$, $R_3$ and $R_3'$ have meaning as defined above; and pharmaceutically acceptable salts thereof.

A preferred embodiment of the invention is directed to (cycloocta, cyclonona, cyclodeca, cycloundeca and cyclododeca)-[b]-pyrazolo[3,4-d]pyridin-3-one derivatives of formula IA wherein A represents hexamethylene, heptamethylene, octamethylene, nonamethylene or decamethylene, respectively, unsubstituted or mono- or di-substituted (on carbon atoms within a said polymethylene chain) by lower alkyl, hydroxy, acyloxy, oxo, lower alkoxy, aryl, aryl-lower alkyl or aryl-lower alkoxy; $R_1$ has meaning as given above; $R_2$ and $R_3$ represent hydrogen; tautomers thereof; and pharmaceutically acceptable salts thereof.

A further preferred embodiment of the invention is represented by the $R_1$-substituted $C_8$-$C_{12}$-cycloalka[b]-pyrazolo[3,4-d]pyridin-3-ones of the formula II

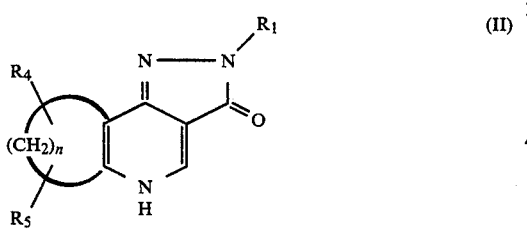

wherein $R_1$ represents lower alkyl, phenyl or phenyl mono- or di-substituted by lower alkyl, lower alkoxy, halogen or trifluoromethyl; or $R_1$ represents an aromatic heterocyclic radical selected from pyridyl, quinolyl, isoquinolyl, pyrimidyl and thiazolyl, or any said radical mono- or di-substituted by lower alkyl, lower alkoxy or halogen; $R_4$ and $R_5$ represent independently hydrogen, lower alkyl, $C_3$-$C_7$-cycloalkyl, hydroxy, acyloxy, lower alkoxy, aryl, aryl-lower alkyl or aryl-lower alkoxy; or $R_4$ and $R_5$ when combined and attached to the same carbon atom represent spiro-fused cyclopentyl or spiro-fused cyclohexyl; n represents the integer 6, 7, 8, 9 or 10; aryl represents phenyl or phenyl mono- or di-substituted by lower alkyl, lower alkoxy, hydroxy, halogen or trifluoromethyl; tautomers thereof; and pharmaceutically acceptable salts thereof.

Specific distinct embodiments of the invention relate to the compounds of the formula II wherein n is either 6, 7, 8, 9, or 10; and $R_1$, $R_4$ and $R_5$ have meaning as defined herein. Preferred are the compounds wherein n represents either 6, 7 or 8, advantageously those wherein n represents 6.

More specifically such relate to (a) the octahydrocycloocta[b]pyrazolo[3,4-d]pyridin3(5H)-one derivatives of formula II when n represents the integer 6;

(b) the decahydrocyclonona[b]pyrazolo[3,4-d]pyridin-3-one derivatives of formula II when n represents the integer 7;

(c) the decahydrocyclodeca[b]pyrazolo[3,4-d]pyridin-3(5H)-one derivatives of formula II when n represents the integer 8;

(d) the dodecahydrocycloundeca[b]pyrazolo[3,4-d]pyridin-3-one derivatives of formula II when n represents the integer 9; and (e) the dodecahydrocyclododeca[b]pyrazolo[3,4-d]pyridin-3(5H)-one derivatives of formula II when n represents the integer 10; and wherein $R_1$, $R_4$ and $R_5$ have meaning as defined above and hereinafter.

Particularly preferred are said compounds of formula II wherein n, $R_4$ and $R_5$ are as defined herein; and (a) wherein $R_1$ is phenyl or phenyl mono- or di-substituted by lower alkyl, lower alkoxy, halogen or trifluoromethyl;

(b) wherein $R_1$ is 2-pyridyl, 5-(methyl, methoxy or chloro)-2-pyridyl, 3-pyridyl, 6-(methyl or methoxy)-3pyridyl or 4-pyridyl;

(c) wherein $R_1$ is 2-pyrimidyl, 5-(methyl, methoxy or chloro)-2-pyrimidyl, 4-pyrimidyl or 5-pyrimidyl;

(d) wherein $R_1$ is 2-thiazolyl or 5-(methyl, methoxy or chloro)-2-thiazolyl;

(e) wherein $R_1$ is 2-quinolyl, 3-quinolyl, or 7-chloro-4-quinolyl;

(f) wherein $R_1$ is straight chain alkyl of 1 to 4 carbon atoms; or (g) wherein $R_1$ is 1-isoquinolyl; tautomers thereof; and pharmacutically acceptable salts thereof.

A further specific embodiment relates to any of the compounds of formula II wherein $R_1$ and n have meaning as defined above; $R_4$ represents hydrogen or lower alkyl; and $R_5$ represents aryl-lower alkyl, aryl-lower alkoxy or $C_5$-$C_7$-cycloalkyl.

Another specific embodiment relates to the above cited compounds of formula II wherein $R_4$ and $R_5$ are attached to the same carbon atom; $R_4$ represents $C_1$-$C_4$ alkyl, advantageously straight chain $C_1$-$C_4$-alkyl; $R_5$ represents $C_1$-$C_4$-alkyl or $C_1$-$C_4$-alkoxy (advantageously straight chain $C_1$-$C_4$-alkyl or alkoxy), hydroxy or acyloxy.

Preferred are compounds of formula II wherein $R_4$ and $R_5$ independently represent hydrogen or lower alkyl.

Particularly preferred are the compounds of formula II wherein n has meaning as defined above; $R_1$ represents phenyl, or phenyl mono- or di-substituted by lower alkyl, lower alkoxy, halogen or trifluoromethyl; $R_4$ and $R_5$ represent hydrogen or lower alkyl; tautomers thereof; and pharmaceutically acceptable salts thereof.

Further preferred are said above compounds of formula II wherein n represents the integers as defined above; $R_1$ represents phenyl or phenyl mono-substituted by lower alkyl, lower alkoxy or halogen; $R_4$ and $R_5$ represent hydrogen or lower alkyl; tautomers thereof; and pharmaceutically acceptable salts thereof.

A particular embodiment relates to said compounds of formula II wherein $R_1$ represents phenyl mono-substituted at the para position by lower alkyl, lower alkoxy or halogen; and $R_4$ and $R_5$ represent hydrogen: tautomers thereof; and pharmaceutically acceptable salts thereof; which are predominantly benzodiazepine receptor agonists. Preferred are the said compounds wherein $R_1$ represents phenyl monosubstituted at the para position by lower alkoxy.

Another particular embodiment relates to the compounds of formula II wherein $R_1$ represents 2-pyridyl; $R_4$ and $R_5$ represent hydrogen; n represents an integer as defined above; tautomers thereof; and pharmaceutically acceptable salts thereof; which are predominantly benzodiazepine receptor antagonists.

The general definitions used herein have the following meaning within the scope of the present invention, including intermediates and starting materials.

The term "lower" referred to above and hereinafter in connection with organic radicals or compounds respectively defines such with up to and including 7, preferably up and including 4 and advantageously one or two carbon atoms.

Halogen is preferably fluoro or chloro, but may also be bromo or iodo.

A lower alkyl group or such present in said lower alkoxy, or other alkylated groups, is above all methyl, but also ethyl n- or i-(propyl, butyl, pentyl, hexyl or heptyl), e.g. 2-methylpropyl or 3-methylbutyl.

Pyridyl represents 2-, 3- or 4-pyridyl, advantageously 2-pyridyl.

Quinolyl represents preferably 2-, 3- or 4-quinolyl, advantageously 3-quinolyl.

Isoquinolyl represents preferably 1-, 3- or 4-isoquinolyl, advantageously 1-isoquinolyl.

Pyrimidyl represents 2-, 4- or 5-pyrimidyl, preferably 2- or 5-pyrimidyl.

Thiazolyl represents preferably 2-thiazolyl.

A lower alkylidene group (with double bond exocyclic to the ring) represents preferably methylidene or ethylidene.

Aryl unless specified otherwise represents preferably phenyl or phenyl mono- or di-substituted by lower alkyl, lower alkoxy, hydroxy, acyloxy, halogen or trifluoromethyl.

Acyloxy is preferably lower alkanoyloxy or aroyloxy. Lower alkanoyloxy is preferably acetoxy or propionyloxy. Aroyloxy is preferably benzoyloxy or benzoyloxy substituted on the benzene ring by one or two of lower alkyl, lower alkoxy, halogen or trifluoromethyl.

Acyloxy may also represent aryloxycarbonyloxy.

Acyl is preferably lower alkanoyl or aroyl, aroyl having meaning as defined above.

The compounds of the invention wherein $R_3$ and $R_3'$ are hydrogen may be represented by either of the tautomeric structures IA or IB, preferably structure IA; furthermore said 3-oxo compounds e.g. of formula II may, under certain conditions, also exist as the 3-hydroxy (enol) tautomers; all of these tautomers are within the scope for the present invention. Said compounds form, especially in the form of the 3-hydroxy compounds, salts with strong bases, and the salts are preferably alkali metal, e.g. sodium or potassium salts of the 1- or 5-unsubstituted compounds ($R_3$ and $R_3'$=H).

Furthermore compounds of Formula IA or IB, form acid addition salts, which are preferably such of pharmaceutically acceptable inorganic or organic acids, such as strong mineral acids, for example hydrohalic, e.g. hydrochloric or hydrobromic acid; sulfuric, phosphoric or nitric acid; aliphatic or aromatic carboxylic or sulfonic acids, e.g. acetic, propionic, succinic, glycolic, lactic, malic, tartaric, gluconic, citric, maleic, fumaric, hydroxymaleic, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, benzenesulfonic, p-toluenesulfonic, naphthalenesulfonic, sulfanilic, cyclohexylsulfamic acid; or ascorbic acid.

The compounds of the invention exhibit valuable pharmacological properties, e.g. nervous system regulatory effects, by inter alia modulating the benzodiazepine receptor activity in mammals. The compounds are thus useful for the treatment of nervous system diseases, e.g. those responsive to benzodiazepine receptor modulation.

The compounds of the invention bind to the benzodiazepine receptor and exhibit e.g. anxiolytic and/or anticonvulsant effects, or antagonism of the effects of benzodiazepine drugs. Said effects are demonstrable by in vitro and in vivo tests, using advantageously mammals, e.g. mice, rats, or monkeys, as test objects. Said compounds can be applied to them enterally or parenterally, advantageously orally, or subcutaneously, intravenously or intraperitoneally, for example, within gelatin capsules or in the form of aqueous solutions or suspensions respectively. The applied dosage may range between about 0.1 and 100 mg/kg/day, preferably between about 0.5 and 30 mg/kg/day, advantageously between about 1 and 25 mg/kg/day. The applied dosage in vitro may range between about $10^{-5}$ and $10^{-10}$ M concentration, preferably between about $10^{-7}$ and $10^{-9}$ M.

The benzodiazepine receptor binding properties indicative of the nervous system regulatory activity of said new compounds are determined in the receptor binding assay in vitro, e.g. similarly to that in Nature 266, 732 (1977) or Proc. Nat. Acad. Sci. USA 74, 3805 (1977). When tritiated flunitrazepam is used, the interaction of other drugs with said receptor can be readily assessed thus: Synaptosnal membranes from rat forebrain are incubated at 0°–5° for 30 minutes with 0.5 nM tritiated flunitrazepam and various concentrations of the test substance in a buffer medium maintained at pH 7.5. Solutions of the various concentrations of test substance are prepared by dilution of a 4.2 mM stock solution in dimethylacetamide-ethanol (1:10) with 50 mM pH 7.5 Tris-HCl buffer. The membranes, containing the receptors with various amounts of tritiated flunitrazepam, are filtered onto glass fiber filters, which are then analyzed in a liquid scintillation counter. The concentration of the compounds of this invention, required to inhibit the specific binding of 0.5 nM of tritiated flunitrazepam by 50%, i.e. the $IC_{50}$, is determined graphically.

In vivo benzodiazepine receptor binding is determined essentially as described in Eur. J. Pharmacol. 48, 213 (1978) and Nature 275, 551 (1978).

Test compounds in a corn starch vehicle are administered orally or intraperitoneally to mice or rats. Thirty minutes later, $^3$H-flunitrazepam (2 nmoles/Kg in saline) is injected into the tail vein, and the animals are sacrificed 20 minutes after injection of the flunitrazepam. The brains are then assayed by determining radioactivity in a liquid scintillation counter for binding of the radioligand to the receptors. A decrease in the binding of $^3$H-flunitrazepam in the drug-treated animals (as compared with the binding observed in animals treated with vehicle alone) is indicative of benzodiazepine receptor binding by the test compound.

Anxiolytic effects are observed, for example, by measuring the antagonism of pentylenetetrazol discriminative stimuli in the rat and according to the Cook-Davidson conflict procedure, using male Wistar rats, e.g. as described in Drug Development Research 6: 313–325 (1985).

Anticonvulsant effects are observed, for example in the standard Metrazole (pentylenetetrazole) and audiogenic seizure tests in the rat for assessing anticonvulsant activity, e.g. as described in Drug Development Research 6: 313–325 (1985).

Benzodiazepine antagonism can be determined by measuring by the antagonism of the anticonvulsant activity of diazepam in the rat Metrazole model, or by measuring the antagonism of diazepam in the rat rotorod procedure, e.g. as described in Drug Development Research 6: 313–325 (1985).

Inverse agonist activity can be determined e.g. by measuring the potentiation of metrazole in the rat metrazole model.

The pharmacological agonist and/or antagonist/inverse agonist profile of the benzodiazepine receptor modulators of the invention can also be determined by measuring their effect in a rat brain membrane preparation on the displacement of $^3$H-flunitrazepam in the presence or absence of gamma-aminobutric acid (GABA), on the enhancement of $^3$H-muscimol binding by etazolate, or on the binding of $^{35}$S-butyl bicyclophosphorothionate (TBPS), e.g. as described in J. Pharmacol. Exp. Ther. 231, 572 (1984).

The compounds of the invention which bind to the benzodiazepine receptor and demonstrate a benzodiazepine agonist profile are most useful as anxiolytic and as anticonvulsant agents for the treatment of anxiety and convulsive disorders, particularly petit mal epilepsy. Illustrative thereof are the compounds of examples 1 and 2b.

Compounds of the invention which demonstrate a benzodiazepine agonist profile exhibit anxiolytic activity, e.g. in the Cook-Davidson conflict procedure, while being essentially free of effects such as sedation, tolerance, interaction with alcohol, and muscle relaxation seen with classical anxiolytic agents such as diazepam.

Sedative effects are determined e.g. in the standard rotorod performance test and alcohol interaction is determined e.g. in the rotorod alcohol interaction test in the rat.

Compounds of the invention which are benzodiazepine agonists and demonstrate anxiolytic properties, e.g. as determined in the Cook-Davidson model, also do not generalize to the discrimination test in the rat which is carried out according to Drug Development Research 6, 313–325 (1985) and in which test compounds are administered orally. Illustrative thereof is the compound of example 1.

The diazepam discrimination test, can also be used to determine benzodiazepine antagonist properties.

The compounds of the invention which bind to the benzodiazepine receptor and demonstrate a benzodiazepine antagonist/inverse agonist profile are most useful as somnolytics, as enhancers of cognitive performance and vigilance, and as appetite suppressants for the treatment of e.g. depression and obesity.

Accordingly, the compounds of the invention are useful nervous system active agents, e.g. as benzodiazepine receptor modulators, for example in the treatment or management of nervous systems disorders in mammals responsive to said modulation. They are also useful in the preparation of other valuable products, especially of pharmacologically active pharmaceutical compositions.

The compounds of the invention, i.e. the compounds of formula IA or IB and salts, or tautomers thereof, are advantageously prepared according to the following processes:

(a) reacting a compound of formula III

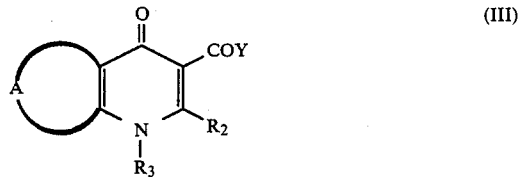

wherein A, $R_2$ and $R_3$ have meaning as previously defined, and Y is lower alkoxy; with a compound of formula IV $$R_3'{-}NH{-}NH{-}R_1 \qquad (IV)$$

wherein $R_1$ has meaning as previously defined, and $R_3'$ is hydrogen; or (b) reacting a compound of the formula V

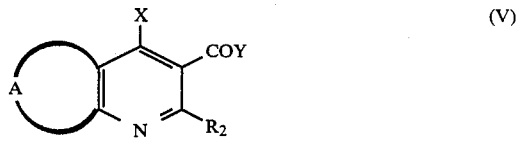

wherein A and $R_2$ have meaning as previously defined; X represents reactive etherified or esterified hydroxy; and Y represents lower alkoxy; with a compound of formula IV wherein $R_1$ has meaning as previously defined, and $R_3'$ represents hydrogen or lower alkyl; or (c) cyclizing a compound of formula V above, wherein X is -$NR_3'$-$NHR_1$ and Y is lower alkoxy or hydroxy; or X is hydroxy, reactive esterified or etherified hydroxy, and Y is —$NR_1NHR_3'$; and wherein A, $R_1$, $R_2$ and $R_3'$ have meaning as previously defined; or (d) cyclizing a compound of formula V wherein X is lower alkoxyamino or azido and Y is —NH—$R_1$, and A, $R_1$ and $R_2$ have meaning as previously defined; or (e) cyclizing a compound of formula VI

wherein W is hydrogen, Z is

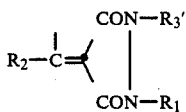

and A, $R_1$, $R_2$, $R_3$ and $R_3'$ have meaning as previously defined; or (f) cyclizing a compound of formula VI above wherein

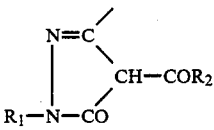

or an enamine derivative thereof, and Z is hydrogen, and A, $R_1$, $R_2$ and $R_3$ have same meaning as previously defined; or (g) cyclizing a compound of formula VI above wherein W is

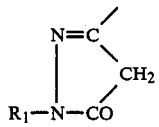

Z is $R_2CO—$, or

is isocyano, and A, $R_1$, $R_2$, and $R_3$ have same meaning as previously defined; and if desired, converting a resulting compound of formula IA or IB into a salt thereof or liberating a free compound from such a salt; or converting a resulting compound into another compound of the invention.

The condensation according to process (a) is carried out preferably at a temperature range of about 50° to 180°, advantageously in the presence of inert solvents such as aliphatic or aromatic hydrocarbons and ethers such as toluene, xylene, biphenyl and/or diphenyl ether, advantageously e.g. while distilling off the alkanol and water generated, or in the presence of dehydrating agents, such as molecular sieves.

The starting materials of formula III may be prepared by methods analgous to e.g. U.S. Pat. No. 3,429,887 and as described in the examples herein.

The starting materials of formula IV are known or are prepared by methods well known to the art.

The condensation according to process (b) above is carried out with the excess or equivalent amount of a compound of formula IV advantageously and depending on the nature of the reactants at temperatures between about 50° and 200° and preferably in a inert solvent e.g. a lower alkanol such as amyl alcohol, n-butyl alcohol or ethanol, an amide such as dimethylformamide or N-methylpyrrolidinone, an aliphatic or aromatic hydrocarbon such as toluene, xylene or biphenyl, an aromatic ether such as diphenyl ether or mixtures thereof.

The starting materials of formula V may be prepared by methods analgous to U.S. Pat. No. 3,786,043 and as described in the examples herein.

In starting materials of formula V and VIII (below), when X represents reactive esterified hydroxy said group is preferably halogen such as chloro or bromo, or lower alkanesulfonyloxy such as methanesulfonyloxy, or when X represents reactive etherified hydroxy said group is preferably lower alkoxy such as methoxy, or aryloxy such as phenoxy.

The ring closure of compounds of formula V according to process (c) is carried out preferably at a temperature range of about 50° to 200°, advantageously in the presence of inert solvents such as aliphatic or aromatic hydrocarbons, such as toluene, xylene or biphenyl, ethers such as diphenyl ether, alkanols such as n-butanol, with or without a base (such as an alkali metal alkoxide, e.g. sodium ethoxide), a dehydrating agent (such as molecular sieves) or a condensing agent (such as N-ethoxy-carbonyl-2-ethoxy-1,2-dihydroquinoline), depending on the nature of X and Y.

Advantageously a condensing agent or dehydrating agent is used for the ring closure of compounds of formula V wherein Y represents hydroxy.

The starting materials for process (c) of formula V, wherein X is $—NR_3'—NHR_1$ and Y is lower alkoxy or hydroxy, may be obtained by condensation of a compound of formula V, wherein X represents reactive etherified or esterified hydroxy and Y represents lower alkoxy, with a hydrazine of formula IV, wherein $R_1$ and $R_3'$ are as previously defined, in an inert solvent, preferably at a temperature range of about 0° to 75°, and hydrolysis if so required.

The hydrazide starting materials of formula V wherein X is hydroxy, esterified or etherified hydroxy and Y is $—NR_1NHR_3'$, are advantageously prepared by condensing a compound of formula VIII

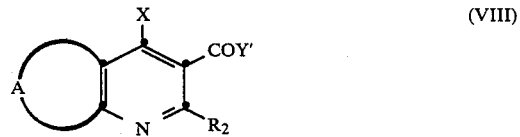

wherein X represents hydroxy, esterified or etherified hydroxy, COY' represents a reactive functionalized carboxy group (such as an acid halide or a mixed anhydride group) and A and $R_2$ are as previously defined, with a hydrazine of formula IV or with an $NHR_3'$-acylated derivative thereof (such as $HNR_1 —NR_3'—COCF_3$) wherein $R_1$ and $R_3'$ are as previously defined, and subsequently deacylating the resulting acyl-substituted hydrazide.

A preferred starting material of formula VIII is the appropriately ring-fused and substituted compound of formula VIII wherein X and Y' represent chloro.

The ring closure of compounds of formula V according to process (d) is preferably carried out by heating them to temperatures between about 120° and 300°, preferably between 200° and 250°, advantageously also in the presence of above-cited inert solvents, e.g. eutectic diphenyl ether-biphenyl.

The starting materials for process (d) of formula V are preferably obtained by condensing 4-halo-cycloalka[b]-pyridine-3-carboxylic acid halides with an $R_1$-amine, and subsequently with a O-lower alkyl-hydroxylamine (a lower alkoxyamine) or an alkali metal azide.

The starting materials for process (d) of formula V may also be prepared from the compounds of formula IX

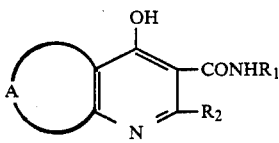

or tautomers thereof, wherein A, $R_1$ and $R_2$ have meaning as previously defined for the compounds of formula IA, by derivatization first to the corresponding 4-halo-cycloalka[b]-pyridine derivatives and subsequently to the compounds of formula V wherein X is lower alkoxyamino or azido, and Y is $—NHR_1$.

The compounds of formula IX are in turn prepared e.g. by condensation of the compounds of formula V wherein A and $R_2$ have meaning as defined above, X represents hydroxy and Y represents lower alkoxy, with an amine $R_1—NH_2$ wherein $R_1$ has meaning as previously defined above, under aminolysis conditions well-known in the art, preferably in the presence of a base such as triisobutylaluminum, advantageously at about room temperature, in an inert solvent such as tetrahydrofuran, methylene chloride or toluene.

The compounds of formula IX, alkali metal salts and acid-addition salts thereof derived from pharmaceutically acceptable inorganic or organic acids as given above in connection with acid addition salts of compounds of formula IA or IB, exhibit benzodiazepine-receptor modulating activity and are thus useful for the treatment of nervous system diseases, such as anxiety and convulsive conditions. Benzodiazepine receptor binding, anxiolytic, anticonvulsant activity or benzodiazepine antagonist/inverse agonist or agonist profile activity are determined in vitro and in vivo using methodology as described above for the compounds of formula IA or IB.

For the in vitro receptor binding assay procedures, the compounds of formula IX are aplied at a concentration ranging from about $10^{-5}$ M to about $10^{-9}$ M. For in vivo tests, the applied dosage may range between about 0.1 and 200 mg/Kg/day, preferably between about 0.5 and 50 mg/Kg/day, advantageously between about 1 and 30 mg/Kg/day.

Preferred are the compounds of formula IX wherein A together with the two carbon atoms to which it is attached represents a fused ring in which A represents hexamethylene, heptamethylene, octamethylene, nonamethylene or decamethylene, each unsubstituted or mono- or di-substituted on carbon atoms within A by lower alkyl, hydroxy, acyloxy, oxo, lower alkoxy, aryl, aryl-lower alkyl or aryl-lower alkoxy; $R_1$ represents lower alkyl, phenyl or phenyl mono- or di-substituted by lower alkyl, lower alkoxy, halogen or trifluoromethyl; or $R_1$ represents pyridyl, quinolyl, isoquinolyl, pyrimidyl or thiazolyl; and $R_2$ represents hydrogen; and pharmaceutially acceptable salts thereof.

The cyclization of compounds of formula VI according to process (e) is preferably carried out with strong aprotic condensation agents, such as polyphosphoric acid lower alkyl esters, advantageously in the presence of inert solvents such as halogenated aliphatic hydrocarbons, e.g. 1,1,2,2-tetrachlorethane.

The starting materials for process (e) of formula VI as defined above for process (e) can be prepared according to known methods, e.g. by condensing a 1-aryl-pyrazolidin-3,5-dione with a starting material of formula VI wherein W is hydrogen and Z is formyl. Said N-formylenamine derivatives useful as starting materials are prepared e.g. as described in Compt. Rend. 264, 333 (1967).

The cyclization of compounds of formula VI according to process (f) is preferably carried out in the presence of conventional molecular sieves, and/or a catalytic amount of acid, e.g., hydrogen chloride A modification of process (f) involves the cyclization of a compound of formula VI wherein W represents the enamine grouping

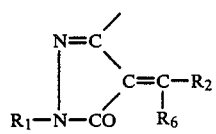

wherein $R_6$ represents e.g. di-lower alkylamino, piperidino or morpholino; A, $R_1$, $R_2$ and $R_3$ have meaning as previously defined; and Z represents hydrogen.

A further modification of process (f) involves the condensation of a compound of formula VI wherein $R_3$ and Z together with the nitrogen to which they are attached represent e.g. di-lower alkylamino, piperidino or morpholino, and W represents the enamine grouping cited just above, with the amine $R_3—NH_2$ preferably in the presence of an acid-addition salt thereof such as the acetic acid salt, preferably in an inert solvent such as ethanol.

The appropriate 3-substituted-pyrazol-5-one starting materials of formula VI as defined for process (f) can be prepared analogous to the process described in Latvijas PSR Zinatnu Akad. Vestis, Kim. Ser. 1965 (5) 587–92, using the suitable intermediates as required for said compounds.

The cyclization of compounds of formula VI according to process (g) is preferably carried out under basic conditions; e.g., in the presence of alkali metal hydroxides, or tertiary organic amines, such as tri-lower alkylamines.

The starting materials of formula VI as defined for process (g) above may be prepared by e.g. dehalogenation of a compound of the formula X

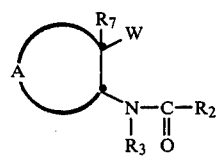

wherein $R_7$ represents halogen, advantageously bromo; and A, W, $R_2$ and $R_3$ have meaning as defined above.

The above intermediates of formula X may in turn be prepared by photochemical addition of e.g. N-bromoformamide or N-bromo-lower alkylcarboxamide [as described in Can. J. Chem. 59, 431 (1981)] to the coresponding ($\alpha,\beta$-unsaturated carbocyclic)-substituted $\beta$-ketoacetic acid lower alkyl ester, followed by condensation with $R_1—NHNH_2$.

The intermediates of formula VI for process (g) wherein $R_2$ and $R_3$ are hydrogen, may, if desired, be dehydrated to the isonitriles with phosphorous halides or phosphorous oxyhalides.

The copmpounds of the invention so obtained can be converted into other compounds of formula IA or IB according to known methods.

For example compounds of formula IA or IB with $R_3$ or $R_3'$=H can be 1-substituted with reactive esters of $R_3$-OH, e.g. such of hydrohalic, aliphatic or aromatic sulfonic acids, such as $R_3$-(halides, sulfates, aliphatic or aromatic sulfonates), e.g. methyl iodide, dimethyl sulfate, methyl mesylate or tosylate, in order to yield the 1-substituted compounds of formula IB. Those of formula IA are similarly obtained from the corresponding alkali metal salts, e.g. the sodium salt, whereby 5-substitution occurs. The metal derivative intermediates are obtained by metallation with reactive organometallic agents such as lithium diisopropylamide, with alkali metal alkoxides such as sodium methoxide, or thallous ethoxide, or alkali metal hydrides such as sodium or potassium hydride.

The compounds with an oxo function within A (ketones) may be converted to the corresponding compounds with a hydroxy function within A (alcohols), e.g. of formula II wherein $R_4$ or $R_5$ represents hydroxy, by reduction, e.g. with a metal hydride reducing agent such as sodium borohydride. Said ketones may also be converted to the tertiary alcohols, e.g. to the compounds of formula III wherein $R_4$ and $R_5$ are on the same carbon atom and represent e.g. lower alkyl and hydroxy, by treatment with e.g. a Grignard reagent such as a lower alkyl magnesium halide.

The compounds with a hydroxy function within A, e.g. the compounds of formula II wherein $R_4$ or $R_5$ represents hydroxy, may in turn be converted to the corresponding compounds with an oxo function within A, by treatment with an oxidizing agent such as pyridinium chlorochromate. Said hydroxy compounds may also be converted to the corresponding acyloxy substituted compounds (esters) by esterification methods well-known in the art.

Finally, the compounds of the invention are either obtained in the free form, or as a salt thereof whenever applicable. Any resulting free base can be converted into a corresponding acid addition salt, preferably with the use of pharmaceutically acceptable acid or anion exchange preparation, or any resulting salt can be converted into the corresponding free base, for example, with the use of a stronger base, such as a metal or ammonium hydroxide or a basic salt, e.g. an alkali metal hydroxide or carbonate, or a cation exchange preparation. Said acid addition salts are preferably such of pharmaceutically acceptable inorganic or organic acids described previously.

Compounds of formula IA or IB with $R_3$ or $R_3'$ being hydrogen can also be converted into the corresponding metal salts by e.g. treatment with the alkaline or alkaline earth metal hydroxides or carbonates.

These and other salts, for example, the picrates, can also be used for purification of the bases obtained; the bases are converted into salts, the salts are separated and the bases liberated from the salts.

In view of the close relationship between the free compounds and the compounds in the form of their salts, whenever a compound is referred to in this context, a corresponding salt is also intended, provided such is possible or appropriate under the circumstances.

The compounds including their salts, can also be obtained in the form of their hydrates or include other solvents used for crystallization.

In case mixtures of isomers of any of the above compounds are obtained, these can be separated into the single isomers by methods in themselves known, e.g. by fractional distillation, crystallization and/or chromatography. Any racemic products can be resolved into the individual optical antipodes.

Any basic racemic products or intermediates can be resolved into the optical antipodes, for example, by separation of diastereomeric salts thereof, e.g., by the fractional crystallization of d- or l-(tartrate, dibenzoyltartrate, mandelate or camphorsulfonate) salts.

Any acidic racemic products of intermediates can be resolved by separation of e.g. the d- and l-($\alpha$-methylbenylamine, cinchonidine, cinchonine, quinine, quinidine, ephedrine, dehydroabietylamine, brucine or strychnine)salts.

The above-mentioned reactions are carried out according to standard methods, in the presence or absence of diluents, preferably such as are inert to the reagents and are solvents thereof, of catalysts, condensing or said other agents respectively and/or inert atmospheres, at low temperatures, room temperature or elevated temperatures, preferably near the boiling point of the solvents used, at atmospheric or superatmospheric pressure.

The invention further includes any variant of the present processes, in which an intermediate product obtainable at any stage thereof is used as starting material and the remaining steps are carried out, or the process is discontinued at any stage thereof, or in which the starting materials are formed under the reaction conditions, or which the reaction components are used in the form of their salts or pure isomers. Mainly those starting materials should be used in said reactions, that lead to the formation of those compounds, indicated above as being especially valuable.

In starting compounds and intermediates which are converted to the compounds of the invention in a manner described herein, functional groups present, such as carbonyl (formyl or keto), carboxy, amino and hydroxy groups, may be protected by conventional protecting groups that are common in preparative organic chemistry. Protected carbonyl, carboxy, amino and hydroxy groups are those that can be converted under mild conditions into free carbonyl, carboxy, amino and hydroxy groups without the molecular framework being destroyed or other undesired side reactions taking place. The need and choice of protecting groups for a particular reaction is known to those skilled in the art and depends on the nature of the functional group to be protected (carbonyl group, carboxy group, amino group etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, New York 1973, T. W. Greene, "Protective Groups in Organic Synthesis", Wiley, New York 1984, and also in "The Peptides", Vol. I, Schroeder and Luebke, Academic Press, London, New York 1965, as well as in Houben-Weyl, "Methoden der Organischen Chemie", Vol. 15/1, George Thieme Verlag, Stuttgart, 1974.

The pharmacologically active compounds of the invention are useful in the manufacture of pharmaceutical compositions comprising an effective amount thereof in conjunction or admixture with excipients suitable for either enteral, parenteral or transdermal application.

Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salt and/or polyethyleneglycol; for tablets, also c) binders, e.g. magnesium aluminium silicate, starch paste, gelatin, tragacanth, methylcellulose, sodium carboxymethylcellulose and/or polyvinylpyrrolidone; if desired, d) disintegrants, e.g. starches, agar, alginic acid or its sodium salt, or effervescet mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1 to 75%, preferably about 1 to 50%, of the active ingredient. Suitable formulations for transdermal application include an effective amount of a pharmacologically active compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

The invention also relates to a method of treatment of disorders in mammals responsive to a benzodiazepine receptor agonist or antagonist/inverse agonist advantageously to the method of treatment of nervous system disorders responsive to the action of a benzodiazepine receptor agonist, using an effective amount of a compound of the invention e.g. of formula II, or pharmaceutically acceptable salts of such compounds, as pharmacologically active substances, preferably in the form of above-cited pharmaceutical compositions. The dosage of active compound administered is dependent on the species of warm-blooded animal (mammal), the body weight, age and individual condition, and on the form of administration.

A unit dosage for a mammal of about 50 to 70 kg may contain between about 10 and 200 mg of the active ingredient.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg.

EXAMPLE 1

A mixture of 2.24 g of ethyl 4-chloro-5,6,7,8,9,10-hexahydrocycloocta[b]pyridine-3-carboxylate and 1.16 g of 4-methoxyphenylhydrazine is stirred and heated at reflux under a nitrogen atmosphere for 20 hours in 20 ml of n-butanol. The solvent is then evaporated under reduced pressure and the residual material stirred with 20 ml of 1N sodium hydroxide, ether, and water. The layers are separated, the aqueous phase is extracted with ether and then treated with an aqueous solution of 1.07 g of ammonium chloride. The precipitate is filtered off and washed with water to give 2-(4-methoxyphenyl)-2,3,6,7,8,9,10,11-octahydrocycloocta[b]pyrazolo[3,4-d]pyridin-3(5H)-one, m.p. 275°–277°, the compound of formula II wherein n represents the integer 6, $R_4$ and $R_5$ represent hydrogen, and $R_1$ represents p-methoxyphenyl. Further purification gives m.p. 283°–285°.

The starting material is prepared as follows:

A solution of 139 g of cyclooctanone, 103 g of diethyl aminomethylenemalonate, and 7 g of dichloroacetic acid in 500 ml toluene is refluxed for 60 hours with a water separator under nitrogen atmosphere, then evaporated to dryness. The residual oil is triturated with 1600 ml heptane and the heptane extract evaporated to dryness. The dried material is purified by flash chromatography on a silica gel column with 2% ethyl acetate in methylene chloride as eluent to give a mixture of cyclooctanone and diethyl N-(1-cyclooctenyl)-aminomethylenemalonate.

A solution of 85 g of the mixture of cyclooctanone and diethyl N-(1-cyclooctenyl)-aminomethylenemalonate in 20 ml. of Dowtherm ® (a eutectic mixture of diphenyl ether and biphenyl) is added to 380 ml. Dowtherm ® at 250°–255° under nitrogen. The distillate is collected in a water separator. After 0.5 hour the mixture is cooled to room temperature and solvent is removed under reduced pressure. The residual solid is triturated with ether to give ethyl 5,6,7,8,9,10-hexahydro-4-hydroxycycloocta[b]pyridine-3-carboxylate, m.p. 219°–222°.

A solution of 5 g of ethyl 5,6,7,8,9,10-hexahydro-4-hydroxycycloocta[b]pyridine-3-carboxylate in 20 ml of phosphorus oxychloride is refluxed for one hour and evaporated to dryness under reduced pressure. A solution of the residue in methylene chloride is treated with ice and water, and basified with 10 N sodium hydroxide. The layers are separated, the aqueous phase reextracted with methylene chloride, and the combined organic layers dried with magnesium sulfate, filtered, and solvent removed at reduced pressure to obtain ethyl 5,6,7,8,9,10-hexahydro-4-chlorocycloocta[b]pyridine-3-carboxylate as an oil which solidifies on standing, m.p. 33°–36°.

EXAMPLE 2

(a) Reaction of ethyl 5,6,7,8,9,10-hexahydro-4-chlorocycloocta[b]pyridine-3-carboxylate with phenylhydrazine according to the procedure analogous to that described in example 1 yields 2,3,6,7,8,9,10,11-octahydro-2-phenylcylcoocta[b]pyrazolo[3,4-d]pyridin-3(5H)-one, m.p. 310°–312°.

(b) Similarly prepared is 2-(4-chlorophenyl)-2,3,6,7,8,9,10,11-octahydrocycloocta[b]pyrazolo[3,4-d]-pyridin-3(5H)-one, m.p. 309–311°.

EXAMPLE 3

Octahydrocycloocta[b]pyrazolo[3,4-d]pyridin-3(5H)-one derivatives of formula II, wherein n represents the integer 6, which can be prepared by procedures analogous to those described in example 1, using an appropriately substituted hydrazine and optionally substituted cyclooctanone as starting materials:

| Example | $R_1$ | $R_4$ | $R_5$ | m.p. |
| --- | --- | --- | --- | --- |
| 3/a | 3-pyridyl | H | H | 296–300° |
| 3/b | 2-thiazolyl | H | H | |
| 3/c | 2-pyrimidyl | H | H | |
| 3/d | 6-methyl-3-pyridyl | H | H | |

-continued

| Example | R₁ | R₄ | R₅ | m.p. |
|---|---|---|---|---|
| 3/e | 3-quinolyl | H | H | |
| 3/f | p-fluorophenyl | H | H | 320–322° |
| 3/g | p-methoxyphenyl | 9-CH₃ | H | |
| 3/h | p-chlorophenyl | 7-CH₃ | 11-CH₃ | |
| 3/i | 2-pyridyl | H | H | 180-188° |
| 3/j | p-ethylphenyl | H | H | 296-300° |
| 3/k | p-ethoxyphenyl | H | H | 299-301° |
| 3/l | 4-pyridyl | H | H | >320° |

5-Methylcyclooctanone, the starting ketone for the preparation of compound 3/g is described in Bull. Soc. Chim. France 1972 (5), 2024–7.

3,7-Dimethylcyclooctanone, the starting ketone for the preparation of compound 3/h is described in Zh. Org. Khim. 13 (9), 1894–7 (1977).

EXAMPLE 4

Decahydrocyclonona[b]pyrazolo[3,4-d]pyridin-3-one derivatives of formula II wherein n represents the integer 7 which can be prepared by procedures analogous to those described in example 1, using an appropriately substituted hydrazine and optionally substituted cyclononanone as starting materials:

| Example | R₁ | R₄ | R₅ |
|---|---|---|---|
| 4/a | 3-pyridyl | H | H |
| 4/b | 2-thiazolyl | H | H |
| 4/c | 2-pyrimidyl | H | H |
| 4/d | 6-methyl-3-pyridyl | H | H |
| 4/e | 3-quinolyl | H | H |
| 4/f | p-methoxyphenyl | H | H |
| 4/g | phenyl | H | H |
| 4/h | p-chlorophenyl | H | H |
| 4/i | p-tolyl | H | H |

EXAMPLE 5

Decahydrocyclodeca[b]pyrazolo[3,4-d]pyridin-3(5H)-one derivatives of formula II wherein n represents the integer 8 which can be prepared by procedures analogous to those described in example 1 using an appropriately substituted hydrazine and optionally substituted cyclodecanone as starting materials:

| Example | R₁ | R₄ | R₅ | m.p. |
|---|---|---|---|---|
| 5/a | 3-pyridyl | H | H | |
| 5/b | 2-thiazolyl | H | H | |
| 5/c | 2-pyrimidyl | H | H | |
| 5/d | 6-methyl-3-pyridyl | H | H | |
| 5/e | 3-quinolyl | H | H | |
| 5/f | 2-pyridyl | H | H | |
| 5/g | p-methoxyphenyl | H | H | 143-150° |
| 5/h | p-fluorophenyl | H | H | |
| 5/i | phenyl | H | H | |
| 5/j | p-chlorophenyl | H | H | |
| 5/k | p-methoxyphenyl | 10-OCH₃ | H | |

6-Methoxycyclodecanone, the ketone starting material for compound 5/k is described in J. Org. Chem. 47, 2685–2690 (1982).

EXAMPLE 6

Dodecanhydracycloundeca[b]pyrazolo[3,4-d]pyridine-3-one derivatives of formula II wherein n represents the integer 9, R₄ and R₅ represent hydrogen, which can be prepared by procedures analogous to those described in example 1 using an appropriately substituted hydrazine and cycloundecanone as starting mateials:

| Example | R₁ |
|---|---|
| 6/a | 3-pyridyl |
| 6/b | p-fluorophenyl |
| 6/c | 2-pyrimidyl |
| 6/d | 3-quinolyl |
| 6/e | p-methoxyphenyl |
| 6/f | m-fluorophenyl |
| 6/g | 2-pyridyl |
| 6/h | phenyl |
| 6/i | p-chlorophenyl |

EXAMPLE 7

Dodecahydrocyclododeca[b]pyrazolo[3,4-pyridin-3(5H)-one derivatives of formula II when n represents the integer 10, which can be prepared by procedures analogous to those described in example 1 using an appropriately substituted hydrazine and an optionally substituted cyclododecanone as starting materials:

| Example | R₁ | R₄ | R₅ | m.p. |
|---|---|---|---|---|
| 7/a | 3-pyridyl | H | H | |
| 7/b | p-fluorophenyl | H | H | |
| 7/c | 2-pyrimidyl | H | H | |
| 7/d | 3-quinolyl | H | H | |
| 7/e | p-methoxyphenyl | H | H | 303–307° |
| 7/f | m-fluorophenyl | H | H | |
| 7/g | 2-pyridyl | H | H | |
| 7/h | phenyl | H | H | |
| 7/i | p-chlorophenyl | H | H | 289–292° |
| 7/j | p-methoxyphenyl | 11-OCOCH₃ | H | |

7-Acetoxycyclododecanone, the starting ketone for preparing compound 7/j is described in J. Chem. Soc. Chem. Commun. 1978 (9), 413–414.

The starting ethyl 4-chlorodecahydrocyclododeca[b]-pyridine-3-carbocylate for compounds 7/a-7/i wherein R₄ and R₅ represent hydrogen is prepared from cyclododecanone as follows:

A solution of 50 g of cyclododecanone, 103 g of diethyl aminomethylenemalonate, and 1.8 g of dichloroacetic acid in 300 ml. toluene is refluxed for 72 hours with a water separator under nitrogen, then evaporated to dryness. The residual oil is triturated with heptane and the heptane extract evaporated to dryness. The dried material is purified by flash chromatography on a silica gel column with methylene chloride as eluent to give a mixture of cyclododecanone and diethyl N-(1-cyclododecenyl)-amino-methylenemalonate.

A solution of 10 g of the mixture of cyclododecanone and diethyl N-(1-cyclododecenyl)-aminomethylenemalonate in 25 ml Dowtherm ® is added to 200 ml Dowtherm ® at 250° under nitrogen, collecting distillate in a water separator. After heating for 0.5 hour the mixture is cooled to room temperature and the solvent distilled off under reduced pressure. The residual solid is triturated with ether and dried to give ethyl 5,6,7,8,9,10,11,12,13,14-decahydro-4hydroxycyclododeca[b]pyridine-3-carboxylate, m.p. 182°–90°.

A solution of 2 g of ethyl 5,6,7,8,9,10,11,12,13,14-decahydro-4-hydroxycyclododeca[b]pyridine-3-carboxylate in 25 ml phosphorus oxychloride is refluxed for 2 hours and evaporated to dryness under reduced pressure. The residue is dissolved in methylene chloride, treated with ice and basified with saturated sodium carbonate solution. The layers are separated, the aqueous phase re-extracted with methylene chloride, and the combined organic layers dried with magnesium sulfate, filtered, and evaporated to dryness to obtain ethyl 4-chloro-5,6,7,8,9,10,11,12,13,14-decahydrocyclododeca[b]pyridine-3-carboxylate as an oil.

EXAMPLE 8

(a) Using procedures analogous to those described in Example 1, 4,4,7,7-tetramethylcyclononanone, described in Acta Chem. Scand. 26 (3), 952–960 (1972), can be converted to 2-(4-methoxyphenyl)-2,3,5,6,7,8,9,10,11,12-decahydro-8,8,11,11-tetramethylcyclonona[b]pyrazolo[3,4-d]pyridine-3-one;

(b) Similarly, 4,4,8,8-tetramethyldecanone, described in Acta. Chem. Scand. 26 (3), 952–960 (1972), can be converted to 2-(4-chlorophenyl)-2,3,6,7,8,9,10,11,12,13-decahydro-8,8,12,12-tetramethylcyclodeca[b]pyrazolo[3,4-d]pyridin-3(5H)-one.

EXAMPLE 9

A mixture of 2.00 g of ethyl 4-chloro-5,6,7,8,9,10,11,12-octahydrocyclodeca[b]pyridine-3-carboxylate and 1.12 g of 4-methoxyphenylhydrazine are stirred for eight hours in 20 ml of N-methylpyrrolidinone at 105°. The solution is then diluted with 50 ml of water and twice extracted with ether. The combined ether fractions are extracted twice with 20 ml of 1 N NaOH and the combined alkaline fractions are back-extracted with ether. The alkaline aqueous solution is then treated with an aqueous solution of 2.14 g of ammonium chloride, stirred until a solid forms; the precipitate is filtered off and dried to give 2-(4-methoxyphenyl)-2,3,6,7,8,9,10,11,12,13-decahydrocyclodeca[b]pyrazolo[3,4-d]pyridin-3(5H)-one, m.p. 143°–150°, the compound of example 5/ g.

The starting material is prepared as follows:

A mixture of 25.0 g of cyclodecanone, 60.7 g of diethyl aminomethylenemalonate, 1.54 g of p-toluenesulfonic acid monohydrate in 500 ml xylene is refluxed 2 weeks under argon, collecting the distillate in a Dean-Stark trap. The solution is then decanted and solvent is removed. The residual oil is triturated twice with hexane and the combined hexane extract is concentrated to yield an oil which is flash chromatographed on 600 g of silica gel using 99:1 methylene chloride ethyl acetate as eluent. A forerun containing cyclodecanone is discarded and the fractions containing the product are combined and concentrated to dryness to give diethyl N-(1-cyclodecenyl)-aminomethylenemalonate as an oil.

A solution of 46.0 g of diethyl N-(1-cyclododecenyl)aminomethylenemalonate in 40 ml of Dowtherm ® is added to one liter of Dowtherm ® at 250° under argon, and the distillate is collected in a Dean-Stark trap. After 0.5 hour the mixture is allowed to cool to room temperature and the solvent is distilled off. The residual solid is triturated with ether to give ethyl 4-hydroxy-5,6,7,8,9,10,11,12-octahydrocyclodeca[b]pyridine-3-carboxylate, m.p. 212°–30°.

A mixture of 4.0 g of ethyl 4-hydroxy-5,6,7,8,9,10,11,12-octahydrocyclodeca[b]pyridine-3-carboxylate and 25 ml of phosphorus oxychloride is refluxed under argon for 3 hours and then evaporated to dryness under reduced pressure. A solution of the residue in methylene chloride is treated with ice and water and basified with 10N sodium hydroxide. The layers are separated, the aqueous phase is re-extracted with methylene chloride; the combined organic extract is dried with magnesium sulfate, filtered, and the solvent is removed at reduced pressure to yield ethyl 4-chloro-5,6,7,8,9,10,11,12-octahydrocyclodeca[b]pyridine-3-carboxylate as an oil.

EXAMPLE 10

Preparation of 1,000 capsules each containing 10 mg of the active ingredient:

Formula

| | |
|---|---|
| 2-(4-methoxyphenyl)-2,3,6,7,8,9,10,11-octahydrocycloocta[b]-pyrazolo[3,4-d]pyridin-3-(5H)one | 10.0 g |
| Lactose | 207.0 g |
| Modified starch | 80.0 g |
| Magnesium stearate | 3.0 g |

Procedure

All the powders are passed through a screen with openings of 0.6 mm. Then the drug substance is placed in a suitable mixer and mixed first with the magnesium stearate, then with the lactose and starch until homogeneous. Hard gelatin capsules are filled with 300 mg of said mixture each, using a capsule filling machine.

Analogously capsules are prepared, containing about 10–200 mg of the other compounds disclosed and exemplified herein.

What is claimed is:

1. A compound of the formula

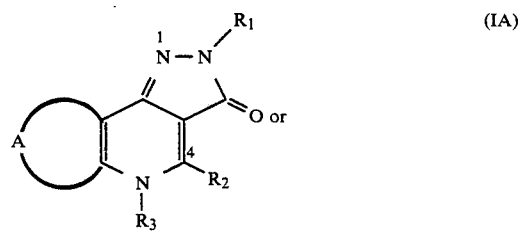

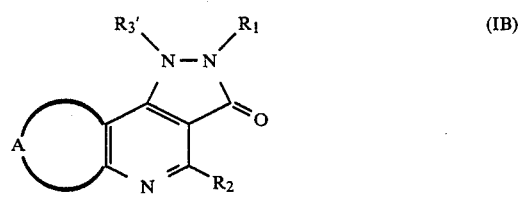

wherein A represents an optionally substituted saturated divalent grouping which togethe with the two carbon atoms to which it is attached represents a fused 8, 9, 10, 11 or 12 membered carbocyclic ring selected from cycloocteno, cyclononeno, cyclodeceno, cycloundeceno and cyclododeceno; each unsubstituted or mono-, di-, tri- or tetra-substituted on carbon atoms within A by lower alkyl, lower alkylident, $C_3$-$C_7$-cycloalkyl, hydroxy, acyloxy, oxo, lower alkoxy, aryl or aryl-lower alkoxy; and when disubstituted on the same carbon atom within A, said carbon atom in each ring is substituted by two lower alkyl or two aryl-lower alkyl groups, or by one lower alkyl or aryl-lower alkyl group and one group selected from hydroxy, lower alkoxy, aryl-lower alkoxy and acyloxy groups; or each ring is disubstituted on the same carbon atom withyin A by straight chain alkylene of 2 to 6 carbon atoms forming with the carbon to which the alkylene chain is attached a spiro-fused 3 to 7 membered ring; or each ring is disubstituted on adjacent carbon atoms within A by alkylene of 3, 4 or 5 carbon atoms to form with the two adjacent carbon atoms to which said alkylene grouping is attached a fused 5-, 6- or 7-membered ring; $R_1$ represents lower alkyl, phenyl, or phenyl mono- or disubstituted by lower alkyl, lower alkoxy, halogen or trifluoromethyl; or $R_1$ represents a heterocyclic radical selected from pyridyl, quinolyl, isoquinolyl, pyrimidyl and thiazolyl, or any of said heterocyclic radicals mono- or disubstituted on carbon by lower alkoxy, lower alkyl or halogen; $R_2$, $R_3$ and $R_3'$ independently represent hydrogen or lower alkyl; aryl within the above definitions represents phenyl or phenyl mono- or disubstituted by lower alkyl, lower alkoxy, hydroxy, acyloxy, halogen or trifluoromethyl; and acyloxy within the above definitions represents lower alkanoyloxy, benzoyloxy or benzoyloxy substituted on the benzene ring by one or two of lower alkyl, lower alkoxy, halogen or trifluoromethyl; a tautomer thereof; or a pharmaceutically acceptable salt thereof.

2. A compound according to claim 1 of formula IA or IB wherein A together with the two carbon atoms to which it is attached represents a fused ring selected from cyclooocteno, cyclononeno, cyclodeceno, cycloundeceno and cyclododeceno in which A represents hexamethylene, heptamethylene, octamethylene, nonamethylene or decamethylene respectively; each said ring unsubstituted or mono-, di-, tri- or tetra-substituted on carbon atoms within A by lower alkyl, lower alkylidene, $C_3-C_7$-cycloalkyl, hydroxy, acyloxy, oxo, lower alkoxy, aryl, aryl-lower alkyl or aryl-lower alkoxy; and when disubstituted on the same carbon atom within A, said carbon atom in each ring is substituted by two lower alkyl or two aryl-lower alkyl groups, or by one lower alkyl or aryl-lower alkyl and one group selected from hydroxy, lower alkoxy, aryl-lower alkoxy and acyloxy groups; or each ring is disubstituted on the same carbon atom within A by ethylene, propylene, butylene or pentylene forming with the carbon to which the alkylene chain is attached a spiro fused cyclopropyl, cyclobutyl, cyclopentyl or cyclohexyl ring; or each ring is disubstituted on adjacent carbon atoms by propylene or butylene to form with the two adjacent carbon atoms to which said alkylene grouping is attac.hed a fused, aryl cyclopentane or cyclohexane ring; $R_1$, $R_2$, $R_3$, $R_3'$ and acyloxy have meaning as defined in said claim; or a pharmaceutically acceptable salt thereof.

3. A compound of the formula

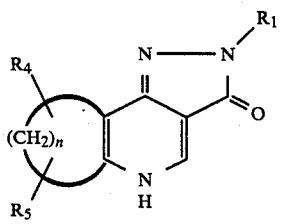

(II)

wherein $R_1$ represents lower alkyl, phenyl or phenyl monoor di-substituted by lower alkyl, lower alkoxy, halogen or trifluoromethyl; or $R_1$ represents an aromatic heterocyclic radical selected from pyridyl, quinolyl, isoquinolyl, pyrimidyl and thiazolyl, or any said radical mono- or di-substituted by lower alkyl, lower alkoxy or halogen; $R_4$ and $R_5$ represent independently hydrogen, lower alkyl, $C_3-C_7$-cycloalkyl, hydroxy, acyloxy, lower alkoxy, aryl, aryl-lower alkyl or aryl-lower alkoxy; or $R_4$ and $R_5$ when combined and attached to the same carbon atom represent spiro-fused cyclopentyl or spiro-fused cyclohexyl; n represents the integer 6, 7, 8, 9 or 10; aryl represents phenyl or phenyl mono- or di-substituted by lower alkyl, lower alkoxy, hydroxy, halogen or trifluoromethyl; acyloxy represents lower alkanoyloxy, benzoyloxy or benzoyloxy substituted on the benzene ring by one or two of lower alkyl, lower alkoxy, halogen or trifluoromethyl; a tautomer thereof; or a pharmaceutically acceptable salt thereof.

4. A compound according to claim 3 wherein n represents the integer 6.

5. A compound according to claim 3 wherein n represents the integer 7.

6. A compound according to claim 3 wherein n represents the integer 8.

7. A compound according to claim 3 wherein n represents the integer 9.

8. A compound according to claim 3 wherein n represents the integer 10.

9. A compound according to claim 3 wherein n represents an integer as defined therein; $R_1$ represents phenyl, or phenyl mono- or di-substituted by lower alkyl, lower alkoxy, halogen or trifluoromethyl; $R_4$ and $R_5$ represent hydrogen or lower alkyl; a tautomer thereof; or a pharmaceutically acceptable salt thereof.

10. A compound according to claim 3 wherein n represents an integer as defined therein; $R_1$ represents phenyl or phenyl mono-substituted by lower alkyl, lower alkoxy or halogen; $R_4$ and $R_5$ represent hydrogen or lower alkyl; a tautomer thereof; or a pharmaceutically acceptable salt thereof.

11. A compound according to claim 10 wherein $R_1$ represents phenyl mono-substituted at the para position by lower alkyl, lower alkoxy or halogen; and $R_4$ and $R_5$ represent hydrogen; a tautomer thereof; or a pharmaceutically acceptable salt thereof.

12. A compound according to claim 3 wherein n represents an integer as defined therein; $R_1$ represents 2-pyridyl; $R_4$ and $R_5$ represent hydrogen; a tautomer thereof; or a pharmaceutically acceptable salt thereof.

13. A compound according to claim 12 wherein $R_1$ represents 2-pyridyl; $R_4$ and $R_5$ represent hydrogen; n represents the integer 6; a tautomer thereof; or a pharmaceutically acceptable salt thereof.

14. A compound according to claim 11 being 2-(4-methoxyphenyl)-2,3,6,7,8,9,10,11-octahydrocycloocta[b]pyrazolo[3,4-d]pyridin-3(5H)-one or a pharmaceutically acceptable salt thereof.

15. A compound according to claim 11 being 2-(4-chlorophenyl)-2,3,6,7,8,9,10,11-octahydrocycloocta[b]pyrazolo[3,4-d]-pyridin-3(5H)-one or a pharmaceutically acceptable salt thereof.

16. A compound according to claim 10 wherein n represents the integer 6, $R_1$ represents phenyl or phenyl mono-or disubstituted by lower alkyl, lower alkoxy, halogen or trifluoromethyl; $R_4$ and $R_5$ represent hydrogen or lower alkyl; a tautomer thereof; or a pharmaceutically acceptable salt thereof.

17. A compound according to claim 11 wherein n represents the integer 6, $R_1$ represents phenyl monosubstituted at the para position by lower alkyl, lower alkoxy or halogen; and $R_4$ and $R_5$ represent hydrogen; a tautomer thereof; or a pharmaceutically acceptable salt thereof.

18. A method of treating anxiety or convulsive disorders in mammals which comprises administering to a mammal in need thereof an effective amount of a compound of claim 11 with benzodiazepine agonist activity or of a pharmaceutical composition comprising an effective amount of a said compound in combination with one or more pharmaceutically acceptable carriers.

19. A method of treating anxiety or convulsive disorders in mammals according to claim 18 which comprises administering to a mammal in need thereof an effective amount of 2-(4-methoxyphenyl)-2,3,6,7,8,9,10,11-octahydrocycloocta[b]-pyrazolo[3,4-d]pyridin-3(5H)-one or a pharmaceutically acceptable salt thereof, or of a pharmaceutical composition comprising an effective amount of a said compound in combination with one or more pharmaceutically acceptable carriers.

20. A method of enhancing cognitive performance and vigilance in mammals which comprises administering to a mammal in need thereof an effective amount of a compound of claim 12 with benzodiazepine antagonist or inverse agonist activity or of a pharmaceutical composition comprising an effective amount of a said compound in combination with one or more pharmaceutically acceptable carriers.

21. A pharmaceutical composition suitable for the treatment of nervous system diseases responsive to a benzodiazepine receptor agonist in mammals comprising an effective amount of a compound of claim 11 in conjunction or admixture with excipients suitable for enteral, parenteral or transdermal application.

22. A pharmaceutical composition suitable for the treatment of anxiety or convulsive disorders in mammals comprising an effective amount of a compound of claim 11 in conjuntion or admixture with excipients suitable for enteral, parenteral or transdermal application.

* * * * *

UNITED STATES PATENT AND TRADEMARK OFFICE
CERTIFICATE OF CORRECTION

PATENT NO. : 4,826,854

DATED : May 2, 1989

INVENTOR(S) : Yokoyama

It is certified that error appears in the above-identified patent and that said Letters Patent is hereby corrected as shown below:

In claim 16, col. 22, line 55.
Correct line 55 to read: ---A compound according to claim 9 wherein n---.

Signed and Sealed this

Twenty-second Day of May, 1990

Attest:

HARRY F. MANBECK, JR.

*Attesting Officer*     *Commissioner of Patents and Trademarks*